US006294327B1

(12) United States Patent
Walton et al.

(10) Patent No.: US 6,294,327 B1
(45) Date of Patent: Sep. 25, 2001

(54) APPARATUS AND METHOD FOR DETECTING SAMPLES LABELED WITH MATERIAL HAVING STRONG LIGHT SCATTERING PROPERTIES, USING REFLECTION MODE LIGHT AND DIFFUSE SCATTERING

(75) Inventors: Ian D. Walton, Redwood City; Mark O. Trulson, San Jose; Richard P. Rava, Redwood City, all of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/013,596

(22) Filed: Jan. 26, 1998

Related U.S. Application Data

(60) Provisional application No. 60/066,432, filed on Nov. 24, 1997, and provisional application No. 60/058,183, filed on Sep. 8, 1997.

(51) Int. Cl.[7] .............................. C12Q 1/68; G01N 21/86; G02B 21/00; G01J 3/00; C07H 21/04
(52) U.S. Cl. ...................... 435/6; 250/559.05; 359/368; 356/300; 536/22.1; 536/23.1; 536/24.3; 536/24.31; 536/24.32
(58) Field of Search ................. 250/559.05; 359/368; 356/300; 435/6; 536/22.1, 23.1, 24.3, 24.31, 24.32

(56) References Cited

U.S. PATENT DOCUMENTS

| 4,961,069 | * | 10/1990 | Tsaprazis | 340/619 |
|---|---|---|---|---|
| 5,379,347 | * | 1/1995 | Kato et al. | 382/8 |
| 5,477,332 | | 12/1995 | Stone et al. | |
| 5,599,668 | | 2/1997 | Stimpson et al. | |
| 5,640,246 | | 6/1997 | Castonguay | |
| 5,680,210 | * | 10/1997 | Swanson | 356/345 |
| 5,841,139 | * | 11/1998 | Sostek | 250/339.12 |

FOREIGN PATENT DOCUMENTS

| 0 411 907 | 6/1991 | (EP) . |
| WO 94/18643 | 8/1994 | (WO) . |

OTHER PUBLICATIONS

EPO Search Authority International Search Report dated Sep. 1997 for PCT/US98/18541.

* cited by examiner

Primary Examiner—Kenneth R. Horlick
Assistant Examiner—Jeffrey Siew
(74) Attorney, Agent, or Firm—Banner & Witcoff, Ltd.

(57) ABSTRACT

A system and method for imaging a sample labeled with a material having a strong light scattering and reflecting properties are provided. A typical material having strong light scattering and reflecting properties is a metal colloid. The imaging system employs a light scattering and reflecting illumination technique. The sample can be imaged with reflection mode imaging along or with a combination of reflection mode and scatter mode imaging.

12 Claims, 8 Drawing Sheets

(1 of 8 Drawing Sheet(s) Filed in Color)

PACKING LIMIT, CHEMICAL SHOT NOISE, AND DYNAMIC RANGE
100 nm IMMUNOGOLD STAINING

PACKING LIMITED DENSITY = 70/MICRON$^2$

LABEL STATISTICAL LIMIT = 50 PARTICLES (S/N=7)
THIS MAY RANGE FROM 10 TO 100 PARTICLES, DEPENDING UPON APPLICATION

| FEATURE SIZE (MICRONS) | PACKING LIMIT (# OF PARTICLES) | THEORETICAL DYNAMIC RANGE |
|---|---|---|
| 200 | 2,800,000 | 56,000 |
| 100 | 700,000 | 14,000 |
| 50 | 180,000 | 3,500 |
| 20 | 28,000 | 560 |
| 10 | 7,000 | 140 |

FIG. 8

APPARATUS AND METHOD FOR DETECTING SAMPLES LABELED WITH MATERIAL HAVING STRONG LIGHT SCATTERING PROPERTIES, USING REFLECTION MODE LIGHT AND DIFFUSE SCATTERING

The present inventors claim priority to U.S. Provisional No. 60/058,183 filed Sep. 8, 1997 and No. 60/066,432 filed Nov. 24, 1997 which are hereby incorporated by reference.

FIELD OF THE INVENTION

The present invention relates to the field of imaging. In particular, the present invention provides a method and apparatus for high resolution imaging of a sample which has been labeled with a material having strong light scattering and/or reflection properties, for example, metal colloid markers. According to the present invention, specific binding analytes are detected by performing imaging using light scattering and reflection illumination.

The present invention is useful in a variety of applications where detection is required. One useful application includes, for example, use with biopolymer arrays. For example, a pioneering technique for creating high density nucleic acid arrays is set forth in U.S. Pat. No. 5,445,934. The present invention is useful in any application in which one can attach a label having strong light scattering and reflection properties to a molecule of interest.

BACKGROUND OF THE INVENTION

The present invention provides a method and instrument for analyzing a sample, such as polymer assays. Examples of such a polymer assay include nucleic acid arrays, protein or polypeptide arrays, carbohydrate arrays, and the like. In addition, the present invention can be used both with samples that are immobilized and in solution. Any number of possible samples can be used with the present invention. Various types of scanners have been used to extract information from a sample. For example, previous instruments for reading samples have employed detection schemes that are responsive to fluorescence in order to reveal specific interactions or hybridizations.

Rather than using fluorescent labeling, it is known to use a solution of particles which scatter light effectively to label nucleic acid arrays. For example, a solution of metal particles, called a metal colloid, could be used. Any other particle which scatters light can also be used to label a sample. More specifically, it is known to detect one or more components of the reaction between a specific binding protein and the corresponding bindable substance, in which one or more labeled components are used, that are obtained by coupling particles of a dispersion of a metal, metal compound or polymer nuclei, as disclosed in U.S. Pat. No. 4,313,734 entitled "Metal Sol Particle Immunoassay."

Further, it is possible to employ a detection method using a two dimensional optical wave guide which allows measurement of real time binding or melting of a light scattering and reflection label at capture zones on a DNA array, as described in "Real Time Detection of DNA Hybridization and Melting on Oligonucleotide Arrays using Optical Wave Guides" by Don I. Stimpson, Joanell V. Hoijer, WangTing Hsieh, Cynthia Jou, Julian Gordon, Tom Theriault, Ron Gamble and John Baldeschwieler.

The above-described document employs a technique for detecting specific binding analytes typically employing a scanning technique that relies on total internal reflectance. This technique is also known in the art as evanescent wave detection. For example, referring to FIG. 1, a cross-section of a transparent array substrate surface of the base of a nucleic acid array is shown. Accordingly, to achieve total internal reflection from the interface of the glass and an aqueous buffer used in the nucleic acid array, the internal incidence angle of light from the scanner must approach 90 degrees. Because the illuminating rays bend toward normal incidence when entering the dense glass chip from air, it is not possible to achieve such a shallow internal incidence angle by simply illuminating nearly parallel to the plane of the transparent array substrate.

With total internal reflectance technology, it is possible to illuminate the sample through the edge of the transparent array substrate. However, this approach is cumbersome and expensive. Moreover, although it may be possible to illuminate the edge of the transparent array substrate with a sample residing in a plastic cartridge, such an arrangement would require that one edge face of the substrate be of fairly high optical quality. This would result in higher packaging costs.

Another possible solution which will allow the use of total internal reflection techniques for reading genetic information from nucleic acid arrays involves the use of a coupling prism which is affixed near the edge of the planar surface. Such a coupling prism allows the illumination to enter the dense transparent array substrate at an angle nearer to normal incidence. Total internal reflection techniques employing a coupling prism require that space be provided for the coupling prism thereby precluding space for probes.

Although total internal reflection techniques may be used with samples in which washing reduces the concentration of residual labels to practically undetectable levels, in such applications, total internal reflection techniques generate undesired background scattering from both the glass/aqueous interface and the glass/air interface.

In addition, other known techniques for labeling with scattering labels tend to bind or react at inappropriate places on the nucleic acid array. For example, metal colloids have been used in blot assays, for example, home pregnancy test kits. Generally, such kits use a colorimetric assay in which colloid agglutination occurs on a white substrate. Test results are determined by light attenuation by the metal colloid which introduces a color.

There exists a need for an apparatus and method for imaging samples which have been labeled with a scattering label having a high scattering signature.

SUMMARY OF THE INVENTION

The present invention is directed to a scanner instrument and method for scanning a sample such as a nucleic acid array by using a novel light scattering and reflection technique. In particular, the combined use of reflection imaging and diffuse scatter imaging has been found to maximize dynamic range and detection limits for samples labeled with scattering labels and bound to nucleic acid arrays. The novel light scattering and reflection technique may be used successfully in various applications because such applications employ a transparent array substrate which exhibits particular optical characteristics, as described below. The sample according to the present invention has been labeled with a scattering label having a strong light scattering and reflection properties. One example of such a scattering label is a metal colloid but the present invention is not limited to the use of a metal colloid and in fact any material with strong light scattering and reflection properties may be used. The present invention does not rely on evanescent wave or total internal reflection techniques. The light scattering and reflection illumination technique of the present invention provides superior optical results to previous methods but at significantly lower cost.

According to a preferred embodiment of the present invention, a light scattering and reflection illumination technique is used for detecting genetic information on a sample in which only reflection mode imaging is used. In another embodiment of the present invention, a sample is imaged through a novel combination of reflection mode imaging and scatter mode imaging. The external incidence angle of light used is typically in a range of angles from near zero to over 45 degrees as measured with respect to the surface normal but any angles may be used.

In addition, an instrument is disclosed which provides imaging according to the novel illumination and collection technique described above.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 8 demonstrates results relating the number of particles, feature size and dynamic range.

DETAILED DESCRIPTION OF THE INVENTION

Figure 1:
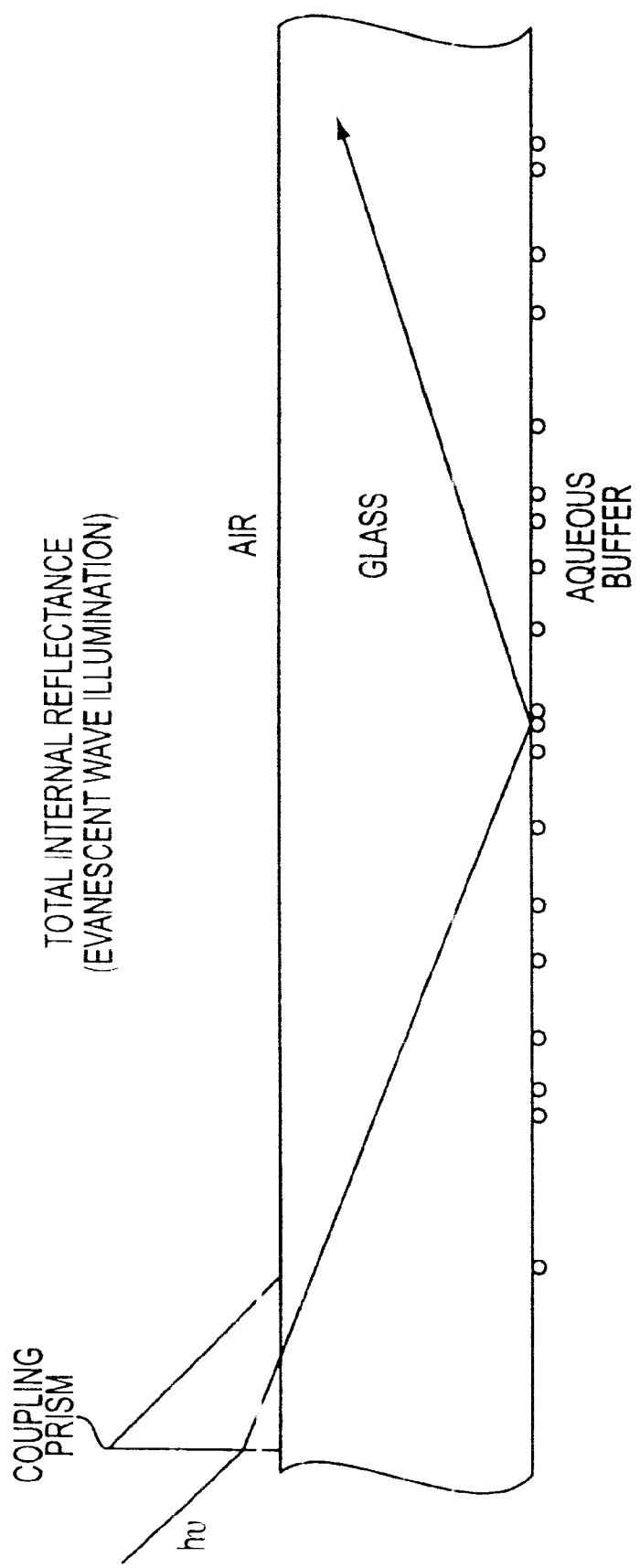
FIG. 1 is a cross-section diagram of a transparent array substrate which illustrates the total internal reflectance detecting technique.

According to the present invention, a novel method and apparatus for imaging samples, such as nucleic acid arrays, is provided in which light scattering and reflection illumination is used. According to a preferred embodiment of the present invention, reflection mode imaging alone is used to image a sample. In a second embodiment, a combination of reflection mode imaging and scatter mode imaging are employed.

An imaging technique known as reflection mode imaging is one in which light is collected from a sample which has been shown onto and reflected from the sample. Said another way, in reflection mode imaging, the light collected is specular. Reflection mode imaging enhances the dynamic headroom by bringing out signals of planar aggregates of scattering labels that have a strong ability to scatter light, such as metal sol labels. As a result, reflection mode imaging works best at the high end of the intensity scale. Although reflection mode imaging produces some reflection background, the present inventors have achieved success in detecting imaging samples solely with the use of reflection mode imaging. On the other hand, in scatter mode imaging, any light collected is light other than that reflected. Thus, the light collected in scatter mode imaging is reemitted light and is non-specular. Scatter mode imaging enhances the dynamic "legroom" by minimizing background signal from the glass/aqueous interface. Thus, scatter mode imaging works best at the low end of the intensity scale. The penalty of this technique is loss of dynamic headroom due to the loss of scattering isotropy at high particle densities. The use of a combination of reflection and scatter mode imaging thus produces the greatest theoretical dynamic range. The present inventors have found such a unique combination of imaging techniques to provide good results.

Particles exhibiting strong light scattering and reflecting properties, called scattering labels, will strongly scatter visible light even though their diameter is quite small, for example, as small as 1/10th the scattered wavelength. Because a sample being scanned according to the present invention is always positioned on a transparent array substrate which has a very high optical quality, and further because the transparent array substrate is in contact with an aqueous buffer which does not scatter much light, almost no diffuse light scattering of any kind occurs as a result of the interface of the transparent array substrate and aqueous buffer with the present invention.

Background from the glass/aqueous interface is negligible in diffuse scattering mode but is measurable with reflection scattering. To minimize any scattering background from the glass/aqueous interface which may occur, it is essential to prohibit the specular reflection from the glass/aqueous interface from entering collecting optics of the scanning instrument. The diffuse scattering geometry permits the detection of exceedingly low surface densities of scattering labels, such as metal sol labels. A disadvantage of such an approach is that at increasingly high particle densities, the spatial distribution of the scattered light becomes less isotropic or diffuse. In the limit of 100% fill factor, the layer of bound gold particles, for example, behaves as a gold mirror, with all "scattered" light emerging from the sample as a pure specular reflection. An optical configuration that detects only diffuse scattering therefore cannot efficiently detect the presence of very high coverages of metal particles and loses dynamic headroom.

Figure 2:
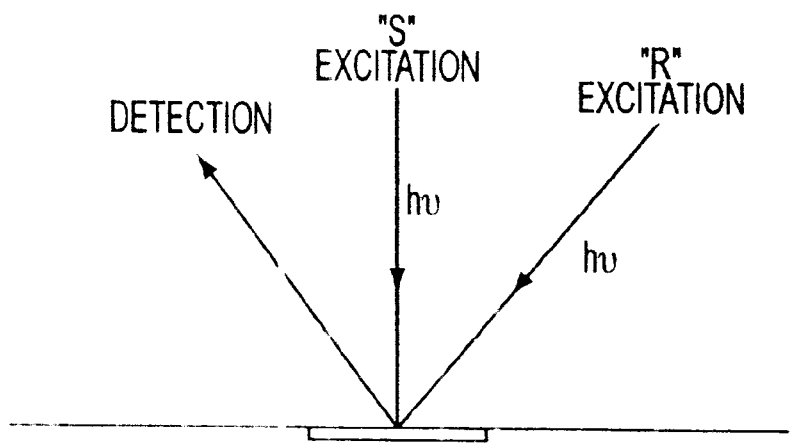
FIG. 2 is a diagram showing two excitation paths reflecting imaging techniques according to the present invention.
Figure 3:
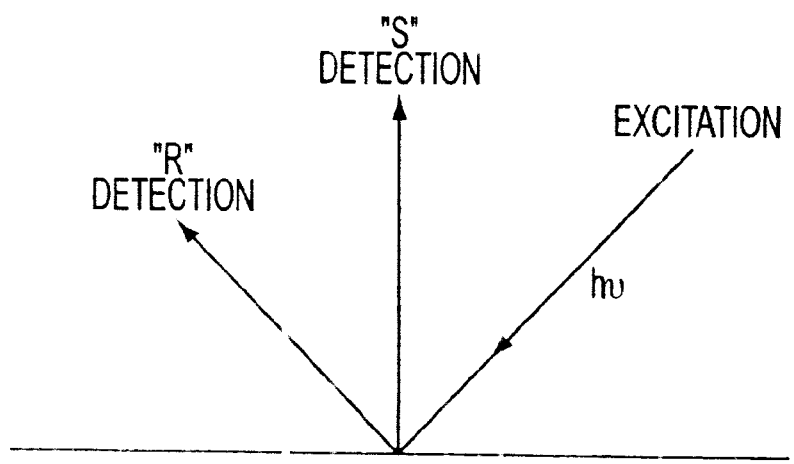
FIG. 3 is a diagram showing two detection paths reflecting imaging techniques according to the present invention.

The method of the present invention is illustrated by reference to FIGS. 2 and 3. Either of two excitation paths shown in FIG. 2 or two detection paths shown in FIG. 3 may be used. The off-axis light paths are depicted at 45 degree angle of incidence, but they are not limited to this value. With either of these configurations, both the diffuse scattering ("S" mode) and specular reflection ("R" mode) may be imaged. The low background scattering encountered in the S mode optimizes the detection of features with low particle densities. In the R mode, the observed signal levels are expected to be much more closely proportional to particle density at the highest attainable densities. The R and S detection modes may therefore be viewed as complementary to one another and together increase the dynamic range of the measurement process.

In the two channel approach, the image data may be acquired and analyzed in at least three ways. First, a single image is generated with simultaneous illumination from R and S sources (FIG. 2). In this case, the intensity of the R source should be substantially lower than that of the S source, in order to minimize its contribution to background reflection. The background generated by the R source may be further reduced by making it in-plane polarized. In the second and third approaches, independent images are generated in S and R modes. The R and S images may be acquired in series with a single detector array (FIG. 2) or in parallel with two detector arrays FIG. 3). An algorithm chooses the intensity data from the two images.

Figure 4:
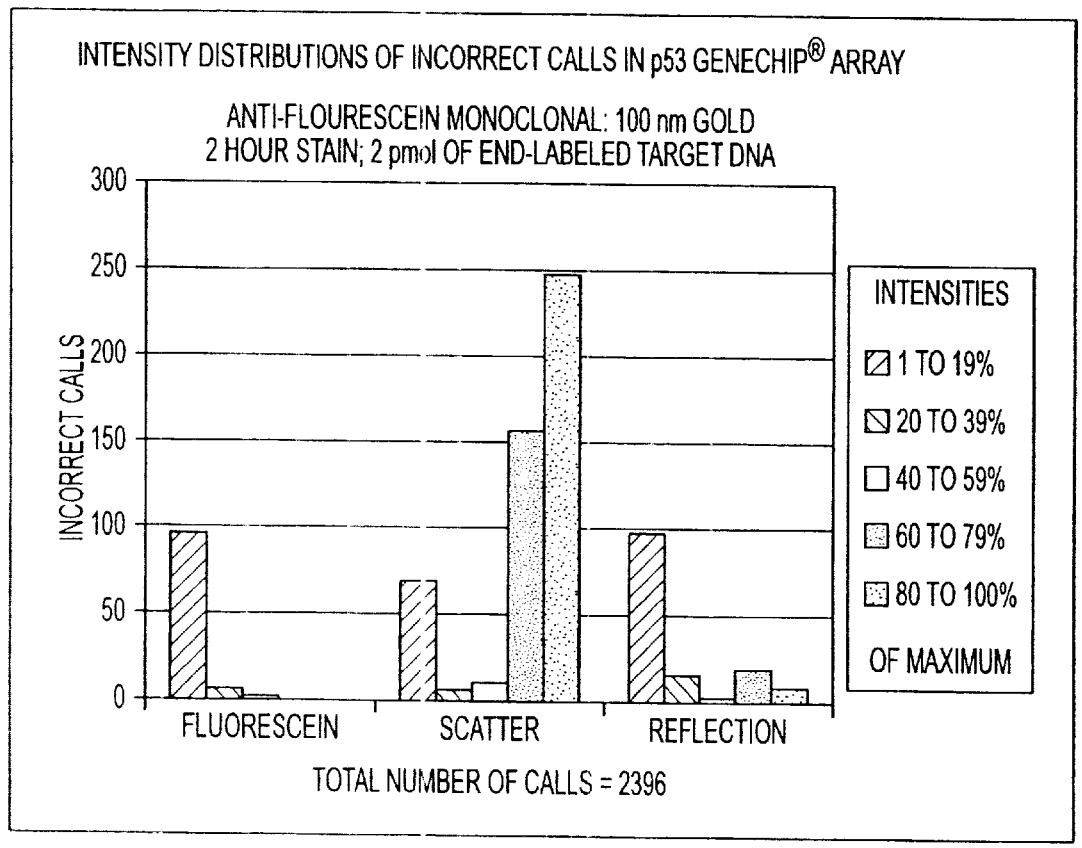
FIG. 4 is a graph comparing results obtained with fluorescent imaging, scatter mode imaging, and reflection mode imaging.

Experiments have been carried out utilizing reflection and scattering mode imaging. The present inventors have found that reflection mode imaging generates very large enhancements in signals, even at particle densities substantially lower than 5/square micron. This enhancement persists to densities well below 1 per square micron. These observations support the notion that clustering of the scattering labels is occurring even at densities in the range of 1 per square micron and that this phenomenon may be exploited to boost signal levels. Thus, the present inventors have found that reflection mode imaging alone may be used to achieve adequate signal to noise over the full dynamic range of the assay. FIG. 4 provides graphic data showing that reflection mode imaging of scattering labels having strong light scattering properties provides results that are as good as imaging performed with fluorescent labeling.

The peak scattered wavelength that can be obtained with the present invention is a function of particle size. For particles up to approximately 50 nm in diameter, the scattering cross sections are proportional to the particle's radius raised to the 6th power and are very large, i.e., $\sim 10^5$ greater than the prior art fluorophores. For larger particles, the present inventors have found a weaker dependence. For example, measurements have determined that 100 nm particles are approximately two times stronger than 80 nm particles.

The inventors of the present invention have determined that good results are obtained when the minimum number of particles used is 50, but the number of particles used may be in a range from 10 to 100 particles, depending on the application. Results relating the number of particles, feature size and dynamic range are found in FIG. 8. The easiest particles to make are gold particles. However, other metals and non-metals may also be used. The mandatory criteria for the particles is that they exhibit a strong light scattering and reflecting signature. Gold is a typical example of a metal used; examples of non-metal which exhibit strong light scattering and reflecting signatures include most semiconductor materials and semi-metals. Because the signal generated by scanning the scattering labels described above is greater than the signal generated with fluorescent labeling, the present invention can be employed using weak light sources for excitation, such as, for example, LEDs, arc amps, and laser diodes.

According to the present invention, the light-scattering particles cannot initially be attached to the sample. Instead, for example, the light-scattering particles are labeled with an anti-body and the target sample is labeled with an antigen that is complimentary to that anti-body. Typically, the target is labeled with Biotin. The light-scattering particle is covalently labeled with Streptavidin or Goat Anti-Biotin.

Figure 5A:
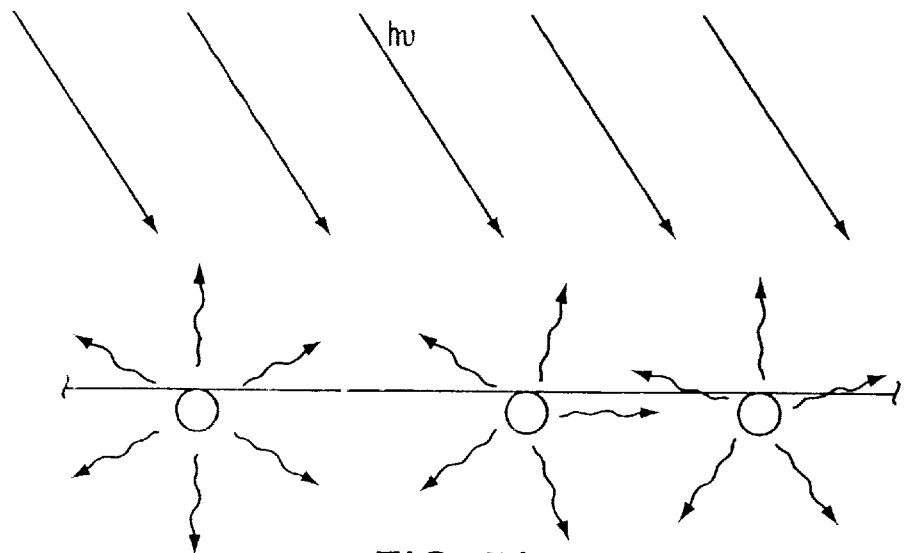
FIG. 5a is a diagram illustrating particle light scattering/reflecting characteristics when particles are loosely packed.
Figure 5B:
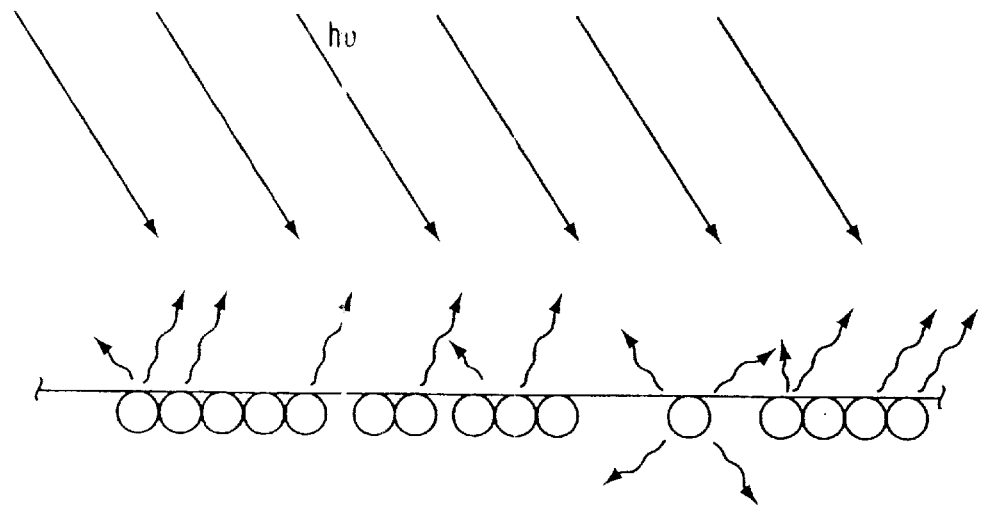
FIG. 5b is a diagram illustrating particle light scattering/reflecting characteristics when particles are densely packed.

As noted, the present inventors have found that excellent results can be achieved with reflection mode imaging alone. Generally speaking, when particles are isolated from one another they tend to scatter light equally in all directions. The present inventors have noted, however, that particles tend to cluster together in a sample's most dense areas. Clustering is also present at densities below $1/\mu m^2$ areas. This clustering of particles creates islands in a planar array on the transparent array substrate which tend to act more like a mirror which, rather than reflecting light in all directions, scatters light in a more specular fashion such that the outgoing light is reciprocal to the incoming light. This phenomena, illustrated in FIGS. 5a and 5b, has greatly limited the dynamic range that could be obtained.

Figure 7:
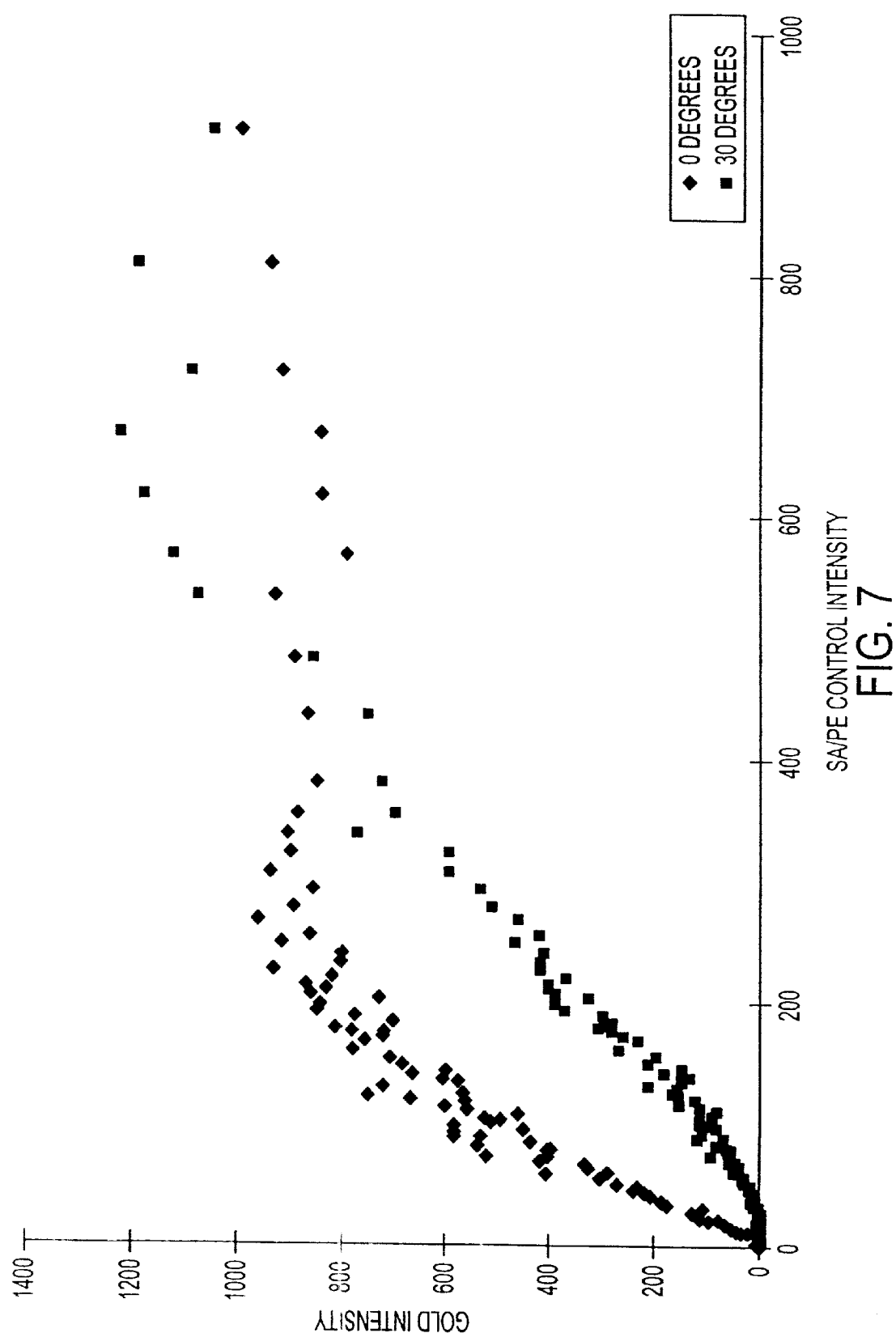
FIG. 7 is a graph depicting the difference between diffuse scatter mode reflection and reflection mode imaging.

Further, the present inventors have discovered that reflection mode imaging of the particles in which the angle of the incident light is the same as the detection angle. Using reflection mode imaging according to the present invention provides enhanced dynamic range which results in superior sensitivity of the scanning instrument as well as ease of use. FIG. 7 is a graph showing the difference in intensity obtained when imaging using a 0 degree angle of illumination with respect to the surface normal (called diffuse scatter mode reflection) and an angle of 30 degrees (reflection mode imaging).

Color multiplexing can be achieved by using particles of different sizes or compositions excited by light source chosen to correspond to peak scattering wavelength of each particle. The scattering bandwidths are broad and so to minimize cross-talk, the wavelength spectral separation between scattering maxima preferably should be twice the width of the band-pass filters used. Wider bandpass results in increased signal. Collection detectors are also filtered, using the same band-pass filters. Spherical scattering labels will substantially maintain the polarization of the incident light upon scattering, and the polarization orientation depends on the incident photon's polarization, not the particle's orientation. Therefore, each excitation channel can be orthogonally polarized. The orthogonal polarizations will reduce cross-talk between channels. Imperfections, scratches and contaminants on the chip will also scatter light and created noise in the detected signal. However, the spectrum of scattering is a function of particle size, and imperfections should have different geometry and hence different scattering spectra. Therefore, the signals received in detection channels can be correlated to minimize background scatter noise.

Reflections from glass/air and glass/water interfaces can be as strong as the scattered signal. Typically, reflection from the glass/air interface is the strongest. In addition, considerable scattering occurs from the back of the cartridge which is made of plastic. These reflections must be spatially rejected by reducing the excitation and/or collection volume of the optical system. Significantly, the present inventors have found that off-axis illumination effectively rejects these reflections. Using off-axis illumination drastically reduces background interferences relative to any imaging method that uses flood illumination and wide field imaging such as CCDs, video cameras, film, etc.

Figure 6:
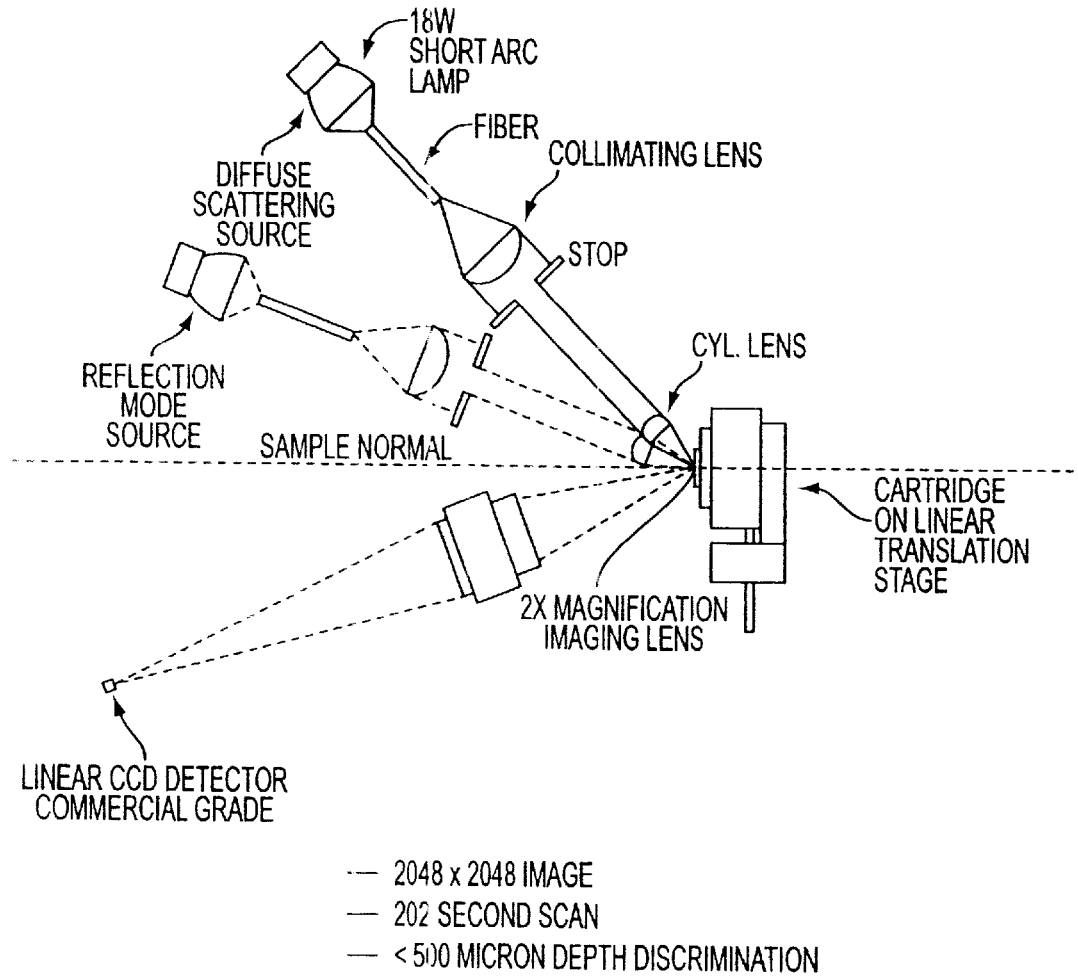
FIG. 6 is a schematic diagram showing a scanning instrument in accordance with the present invention.

FIG. 6 describes an embodiment of the scanner geometry of the present invention. The present inventors have discovered a novel combination of instrumentation elements which provide superior depth resolution. Two light sources are provided in the device, one serving as a reflection mode light source and one serving as a diffuse scattering light source. The illumination is focussed to a line narrow enough to spatially reject unwanted reflections from interfaces. The instrument of the present invention also may include a focussing system and beam shaping optics for excitation.

Scattered light is collected and collimated and optionally may be passed through polarrration analyzers and bandpass filters. However, good results may be obtained without the use of polarizers and bandpass filters which are merely a design choice. The depth of collection should be kept to less than 500 microns FWHM to reject scattering and reflection from the glass/air and plastic aqueous interfaces. As a result, the instrument of the present invention avoids collecting scattered light from other interfaces, for example, from the glass/air interface which allows superior depth resolution. With the present invention, light is collected off of the DNA surface and scattered light from other surfaces is rejected, resulting in superior sensitivity.

A single detector, linear CCD array is used to convert the scattered light image into an electrical signal and each filter/analyzer assembly can be moved in place by a translation stage or wheel. Multiple linear or area CCD arrays can also be used. The labeled surface is scanned across the incident beam using a translation stage. The current from the detector is converted to a voltage which is digitized by an A/D converter. The digital signal is then stored in a computer as an image. The computer controls all functions of the instrument.

It is possible to enhance the dynamic range when employing light scattering and reflecting detection with the instrument of the present invention. The light scattering and reflecting by 100 nm gold particles is roughly isotropic, making it possible to choose a collection angle that excludes the specular reflection from the interface to which the particles are bound, thereby providing a good signal to background ratio at low particle densities. Prototype instruments to detect colloidal gold have utilized illumination at 45 degrees from the array surface normal and detection along the surface normal, or vice versa.

Correlation of light scattering images utilizing 45 degree scattering angle with scanning electron micrographs has established that the effective scattering cross section per particle is constant up to about 5 particles per square micron, above which it drops off rather sharply. Electron microscopy has revealed that this behavior is a consequence of formation of planar aggregates of particles at high densities. With increasing aggregate size, the directional dependence of the scattering changes from the nearly isotropic scattering characteristic of an isolated particle to the pure specular reflection characteristic of a planar layer of gold metal. The scattered light becomes increasingly "concentrated" into a cone centered on the specular reflection angle, leading to an apparent saturation with respect to particle density at observation angles far from the specular reflection angle. This dynamic range saturation has been found to be reduced substantially by employing reflection mode imaging.

Figure 9:
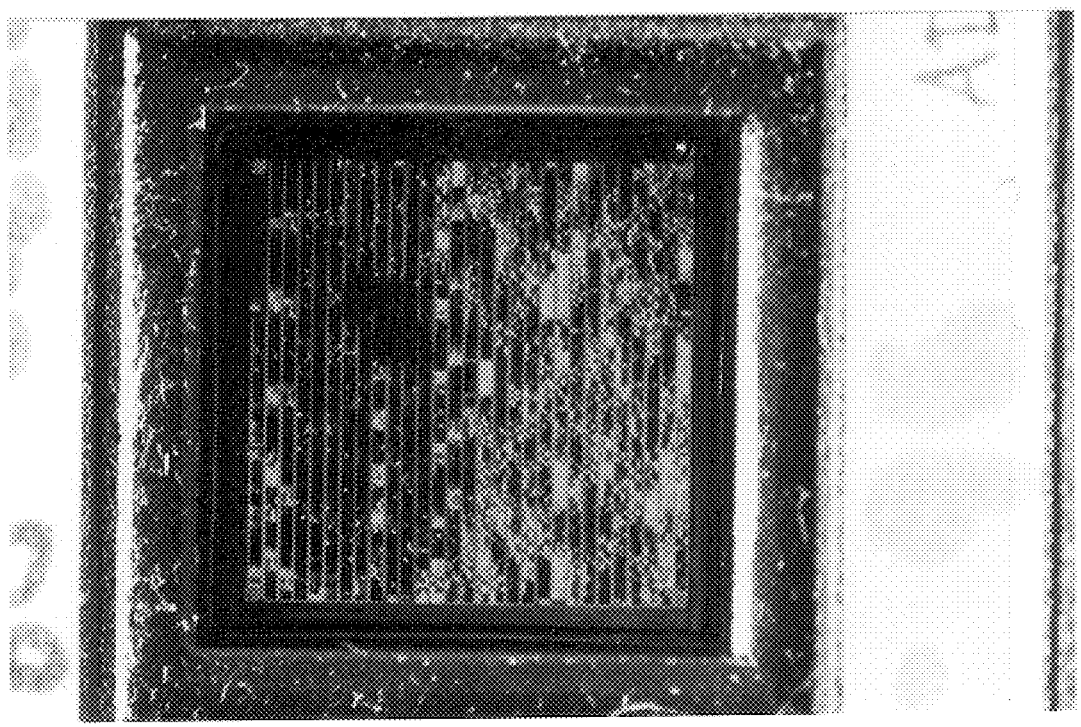
FIG. 9 is a photograph taken with a camera depicting a gene probe array which has been imaged with diffuse scatter mode imaging.

FIG. 9 is an image recorded on film with flood illumination scatter mode imaging and demonstrates how strongly light scattering particles used in the present invention scatter light. FIG. 9 also demonstrates that it is possible to record the spatial distribution of particles with a simple camera.

The present inventors have found that employing illumination at equal and opposite angles, i.e., according to the law of reflection and collection at show nearly complete recovery of signal linearity with respect to fluorescence imaging. It is also possible to customize the illumination method to the specific application, e.g., low signal applications such as gene expression may favor diffuse mode and high signal applications may benefit from reflection mode.

As previously noted, the analysis of samples by hybridization to oligonucleotide arrays is finding widespread applications in biology. Detection of nucleic acid binding to the array has customarily been accomplished by fluorescent labeling of the analyte DNA and confocal laser scanning fluorescence microscopy. The present invention provides a novel apparatus and method for imaging a sample labeled with a material having a strong ability to scatter light.

The present inventors hereby incorporate by reference all patents and publications referred to in the present application.

We claim:

1. An instrument comprising:
    a first light source providing reflection mode light to a sample;
    a second light source providing diffuse scattering light to said sample;
    a detector; and
    a computer configured to interact with said detector such that said detector detects light reflected from said sample in response to application of light from said first light source and said detector detects reemitted light in response to application of light from said second light source;
    wherein said instrument is configured to cause the first light source to provide reflection mode light to the sample during a first time period, and to cause the second light source to provide diffuse scattering light to said sample during a time period other than said first time period.

2. An instrument as claimed in claim 1 wherein said first light source is positioned at a first angle from a line normal to said sample.

3. An instrument as claimed in claim 2 wherein said detector is positioned at a second angle from said line normal to said sample.

4. An instrument as claimed in claim 3 wherein said first light source is positioned on one side of said line normal to said sample and said detector is positioned on the opposite side of said line normal to said sample.

5. An instrument as claimed in claim 4 wherein said detector is positioned on the same side of said line normal to said sample as said first light source.

6. An instrument as claimed in claim 5 wherein said second angle is the same numeric value as said first angle.

7. A method of imaging a sample comprising:
    projecting reflection mode light from a first light source onto said sample during a reflection mode time period;
    detecting light on a detector from said first light source which has been reflected from said sample;
    projecting diffuse scattering light from a second light source onto said sample during a time other than said reflection mode time period; and
    detecting reemitted light on said detector from said sample.

8. A method of imaging a sample comprising:
    projecting diffuse scattering light from a first light source onto said sample;
    detecting on a detector all light except light reflected from said sample in the form of a first signal;
    converting said first signal to a first voltage;
    digitizing said first voltage by an A/D converter;
    storing said digitized first voltage as an image in a computer;
    projecting reflection mode light from a second light source onto said sample;

detecting on said detector light from said second light source which has been reflected from said sample in the form of a second signal;

converting said second signal to a second voltage;

digitizing said second voltage by said A/D converter;

storing said digitized second voltage as an image in said computer.

9. An instrument comprising:

a first light source providing reflection mode light to a sample;

a second light source providing diffuse scattering light to said sample;

a first detector for receiving light reflected from said sample in response to application of light from said first light source; and a second detector for receiving reemitted light in response to application of light from said second light source.

10. The method of claim 7, further comprising the step of providing a sample having a scattering label.

11. The method of claim 10, wherein said scattering label comprises a metal colloid.

12. The method of claim 10, wherein said sample comprises a nucleic acid array.

* * * * *

UNITED STATES PATENT AND TRADEMARK OFFICE
CERTIFICATE OF CORRECTION

PATENT NO. : 6,294,327 B1
DATED : September 25, 2001
INVENTOR(S) : Ian D. Walton et al.

It is certified that error appears in the above-identified patent and that said Letters Patent is hereby corrected as shown below:

Title page,
Item [54], Title, delete
"APPARATUS AND METHOD FOR DETECTING SAMPLES LABELED WITH MATERIAL HAVING STRONG LIGHT SCATTERING PROPERTIES, USING REFLECTION MODE LIGHT AND DIFFUSE SCATTERING" and insert
-- APPARATUS AND METHOD FOR DETECTING SAMPLES LABELED WITH MATERIAL HAVING STRONG LIGHT SCATTERING PROPERTIES, USING REFLECTION MODE LIGHT AND DIFFUSE SCATTERING LIGHT --.

Signed and Sealed this

Twenty-first Day of January, 2003

JAMES E. ROGAN
*Director of the United States Patent and Trademark Office*